United States Patent [19]

Lilienfeld

[11] 4,320,975
[45] Mar. 23, 1982

[54] PASSIVE SMOKE PLUME OPACITY MONITOR

[75] Inventor: Pedro Lilienfeld, Lexington, Mass.

[73] Assignee: GCA Corporation, Bedford, Mass.

[21] Appl. No.: 104,314

[22] Filed: Dec. 17, 1979

[51] Int. Cl.³ .......................................... G01N 21/84
[52] U.S. Cl. .................................. 356/364; 356/341; 356/438
[58] Field of Search ............... 356/364, 365, 366, 367, 356/369, 337, 338, 341, 438; 340/630

[56] References Cited

U.S. PATENT DOCUMENTS

| T947,008 | 6/1976 | Hundal | 356/438 |
|---|---|---|---|
| 3,554,655 | 1/1971 | Einstein . | |
| 3,640,626 | 2/1972 | Liskowitz . | |
| 3,841,763 | 10/1974 | Lewis . | |
| 3,868,186 | 2/1975 | Paukert et al. . | |

3,901,602  8/1975  Gravatt .

OTHER PUBLICATIONS

Conner et al. "Optical Properties and Visual Effects of Smoke-Stack Plumes" Office of Air Programs Publication No. AP-30, U.S. Environmental Protection Agency, May 1972.

*Primary Examiner*—R. A. Rosenberger
*Attorney, Agent, or Firm*—Kenway & Jenney

[57] ABSTRACT

In the smoke opacity monitor disclosed herein, a measurement of opacity is obtained by measuring the proportion of polarized light from the background sky which is detectable through the smoke plume. Compensation and normalization is provided to minimize errors generated by illumination of the plume itself and for the overall intensity of the background sky light.

10 Claims, 10 Drawing Figures

PASSIVE SMOKE PLUME OPACITY MONITOR

BACKGROUND OF THE INVENTION

The present invention relates to a method and apparatus for determining and monitoring the opacity of atmospheric pollutants, e.g. a smoke plume at the chimney of the power generating plant, from a remote location and, more particularly, to such a system which is essentially passive, one which does not require the generation and application of radiant energy to the plume as part of the measuring process.

For the most part, the determination of smoke density, e.g. for compliance with environmental legislation requirements, has been mostly subjective. In other words, human observers have been trained to characterize observed smoke plumes based on a prior learning experience. So-called smoke schools are conducted on a regular basis to allow the observers to re-correlate their impressions with actual measurements taken under controlled circumstances. No matter how proficient such observers may become, however, it is readily apparent that the reported observations may be affected by a great many variables beside the actual opacity of the smoke being observed. Not only does the subjective process depend upon the recollection of the observer but the process may also be affected by the state of illumination of the smoke plume and the character of the background against which the plume is observed.

While instruments are available which may be attached to a smoke stack and which will accurately measure smoke opacity, such instruments are not universally employed or available and, further, are subject to failure due to the hostile environment in which they typically operate.

Some attempts have been made to permit remote measurement of smoke plume opacity but these systems have typically employed either the sun as an in-line light source or some other external light source, such as a laser. These requirements for an external light source have typically caused the systems to be difficult to operate and, in some cases, highly unreliable or even dangerous. Further, in many of these systems it was still necessary for a human observer to subjectively make a final measurement or comparison.

Among the several objects of the present invention may be noted that provision of a method and apparatus for measuring the opacity of atmospheric pollutants, such as those contained in a smoke plume; the provision of such a method and system which may be employed remotely from the smoke source; the provision of such a system which is essentially passive, i.e. which does not require the system to apply radiant energy to the plume; the provision of such a method and system which are simple and reliable in operation; and the provision of such a system which is relatively simple and inexpensive. Other objects and features will be in part apparent and in part pointed out hereinafter.

SUMMARY OF THE INVENTION

In accordance with one aspect, the apparatus of the present invention is rendered selective to light which is being transmitted through the smoke plume by principally basing its measurement on the values of polarized light taken both from the background sky and from the plume. While the component of polarized light taken from the plume may be significantly derived from light originating in the background sky and thus be indicative of the extent of transmission through the plume, difficulty can arise if the plume is exceptionally bright. In such a case, even though the light scattered by the plume due to direct illumination may not be significantly polarized on a percentage basis, the absolute value of the polarized component may be large enough to interfere with accurate measurement. This problem would be maximized in the case of a fully illuminated plume of white smoke on a clear day. The polarized component originating from direct illumination of the plume, however, will be typically of neutral hue, i.e. white. In accordance with another aspect of the invention, the contribution of white polarized light is essentially eliminated by subtracting a measurement of the red component of polarized light from the absolute or total value of the blue component of the polarized light. Thus, in the case of both the plume measurement and the background sky measurement, the difference values utilized are indicative of the extent to which the polarized blue component exceeds the polarized red component. The ratio of these values is, in the preferred embodiment, used as a measurement of transmission. This can be expressed as follows.

$$\frac{I_{pb} - I_{pr}}{I_{sb} - I_{sr}}$$

where $I_{pb}$ and $I_{pb}$ are the blue and red components respectively from the plume and $I_{sb}$ and $I_{sr}$ are the blue and red components respectively from the background sky. As to each of these values, it should be understood that only the polarized component is being measured and considered.

For the evaluation of smoke plumes, however, it is typically desired to express the valuation in terms of opacity so that the value of transmissivity is subtracted from unity. The actual output signal utilized in the preferred embodiment of the invention can thus be represented by the following expression.

$$1 - \frac{I_{pb} - I_{pr}}{I_{sb} - I_{sr}}$$

Briefly stated, the system of the present invention operates by measuring the proportion of polarized blue light from the background sky which passes through the plume. Polarized blue light received from an area of sky adjacent the plume is measured as is the polarized blue component received from the plume itself. The value obtained from the plume is normalized in relation to the value obtained from the sky. The normalized value obtained is then indicative of the transmission through the plume.

In accordance with a further aspect of the invention, the value of red polarized light from each of these sources is also measured and subtracted from the respective blue measurement so as to cancel any contribution due to neutral or white light. Again, this compensation tends to make the final measurement less sensitive to light sources other than sky light seen through the plume.

BRIEF DESCRIPTION OF THE DRAWINGS

Corresponding reference characters indicate corresponding parts throughout the several views of the drawings.

DESCRIPTION OF THE PREFERRED EMBODIMENT

As suggested previously, the present invention takes advantage of the fact that daytime sky light is characterized, particularly on clear days, by being both blue and significantly polarized. Light from a smoke plume, however, does not typically have any pronounced hue nor is it usually highly polarized. On the other hand, it should be understood that the plume itself may be highly illuminated and may be in fact brighter than background sky light. This is particularly true of a plume of white smoke on a clear day. As described in greater detail hereinafter, the practice of the present invention involves compensating for these factors so that the resultant measurement is quite accurately an indication of the proportion of light transmitted from the background sky through the smoke plume and is thus usefully correlated with the opacity of the smoke plume. In performing the compensations, the apparatus disclosed utilizes measurements of both the blue and red polarized components of light from both the plume and from an area of sky adjacent the plume. These signals are processed to derive a signal representing opacity of the smoke plume.

Figure 1:
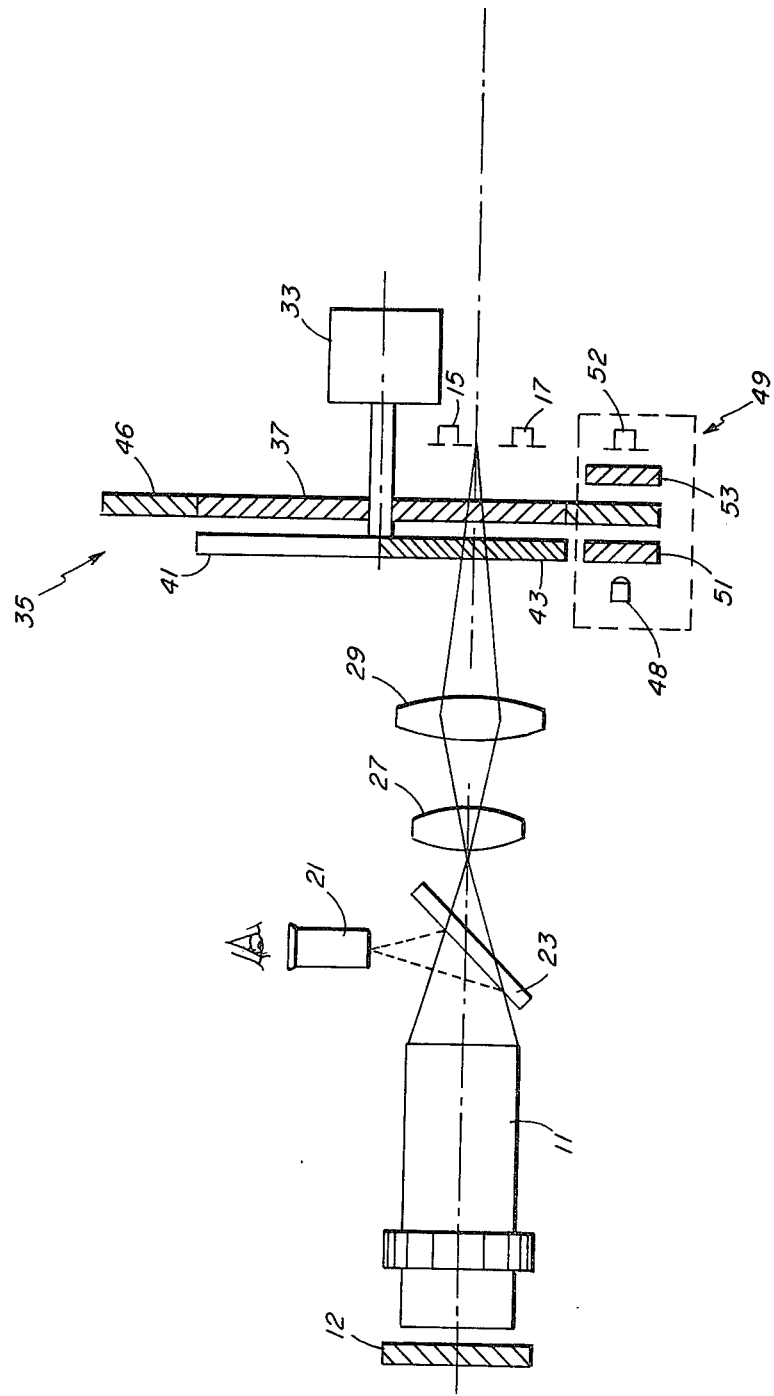
FIG. 1 is a diagram illustrating the arrangement of optical components of a smoke plume opacity monitor constructed in accordance with the present invention.
Figure 2:
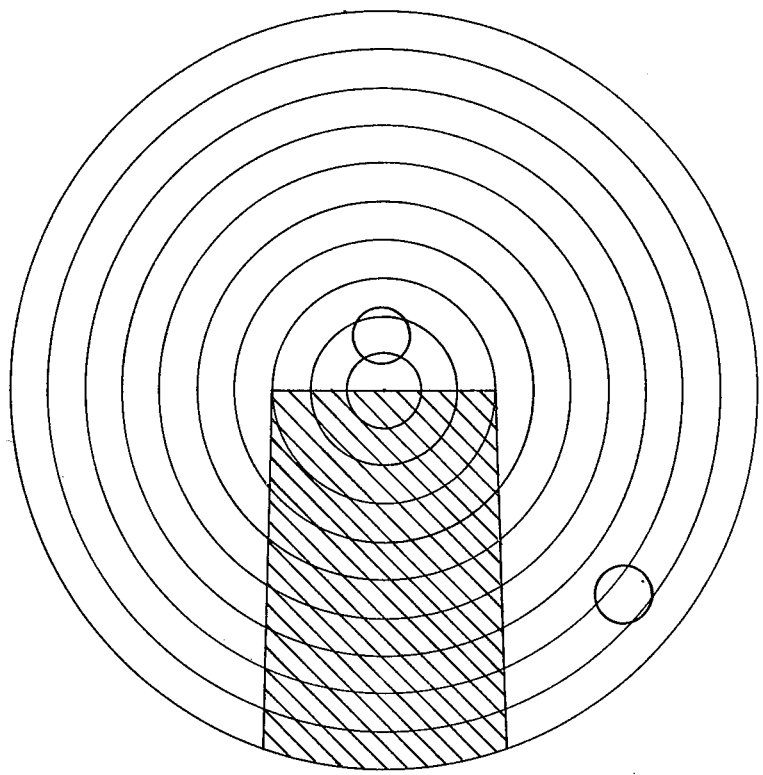
FIG. 2 is a drawing illustrating the view obtained during aiming of the apparatus of FIG. 1, using an eyepiece and reticle incorporated therein and used with an aiming mirror in operative position.

Referring now to FIG. 1, a suitable zoom telephoto lens 11 is provided for collecting light both from a plume to be examined and from background sky. An adjustable, i.e. rotatable, half-wave plate 12 is mounted in front of lens 11. In operation, the light collected by lens 11 is directed onto a pair of photodetectors 15 and 17 which, respectively, view the plume and an adjacent area of sky. However, the system also includes an eyepiece 21 which can be used for accurately aiming the device. An inclined mirror 23 is provided on a manually slidable mount so that it can be selectively positioned in the light path to divert light from the objective lens into the eyepiece 21. Eyepiece 21 preferably includes a reticle carrying indicia appropriately marking the areas in the object field which are observed by the two photodetectors. The view is illustrated in FIG. 2. As shown, the apparatus is aimed so that the detector 15 views an area directly over the stack emitting the plume to be measured while the detector 17 views an adjacent, unobscured area of sky.

When the mirror 23 is drawn out of the way, light from the objective lens 11 is focused by a pair of lenses 27 and 29 onto the two detectors 15 and 17. A motor 33 rotates a filter wheel 35 in front of the detectors. Filter wheel 35 carries both a polarizing disk 37 and a pair of color filters 41 and 43, each of which covers 180 degrees of the wheel's circumference. The filters 41 and 43 each pass light only of a selected wavelength in the red and blue respectively. Thus, each of the detectors 15 and 17 looks alternately at two different color components of the light received from its respective field of view. Further, due to the presence of the rotating polarizing filter 37 adjacent the detectors, the output signal from each detector will be a.c. modulated in accordance with the extent of polarization of the received light. As will be understood by those skilled in the art, these different signal components can be separated electronically so that it is not necessary to have a separate detector for each color component. The presently preferred method of signal processing is described in greater detail hereinafter.

To obtain a reference signal useful in effecting the demodulation and signal separation, a so-called interrupter module 49 is mounted so as to straddle the periphery of the polarizer disk 37. The periphery of the filter wheel comprises an annular half-wave plate 46. Interrupter module 49 is of the type comprising both a light source, an LED 48 and a photodetector such as a light-sensitive diode or phototransistor 52. Fixed polarizers 51 and 53 are mounted in the light path of the interrupter module on either side of the filter wheel. It can thus be seen that, as the motor 33 rotates the filter wheel 35, the interrupter module will generate an a.c. signal which is synchronous with that rotation and can be used as a timing reference for synchronously demodulating the signals obtained from the detectors 15 and 17.

As will be understood by those skilled in the art, the rotation of the filter wheel 35 with the half-wave plate 46 will cause the light received by the phototransistor 52 in the interrupter module to be modulated as a function of the angular relationship of the polarizing elements. As will also be understood by those skilled in the art, the effect of the rotating half-wave plate is to produce two rotations of the angle of polarization of incident light for each rotation of the filter wheel. Further, since the output signal from the photodetector undergoes a minimum each time the angle of polarization is transverse to the fixed polarizer in front of the phototransistor 52, it can be seen that the sinusodial component of the signal from the phototransistor will be at a frequency which is four times the rate of rotation of the filter wheel.

Figure 3A:
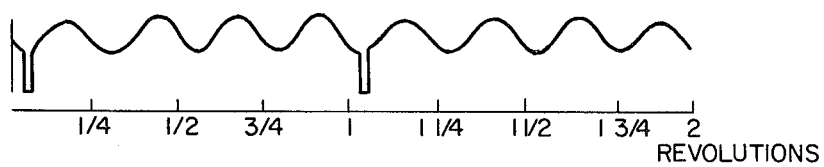
FIGS. 3A–3E represent various signal waveforms generated by detectors in the apparatus of FIG. 1 and occuring in signal processing circuitry which operates on those signals.
Figure 5:
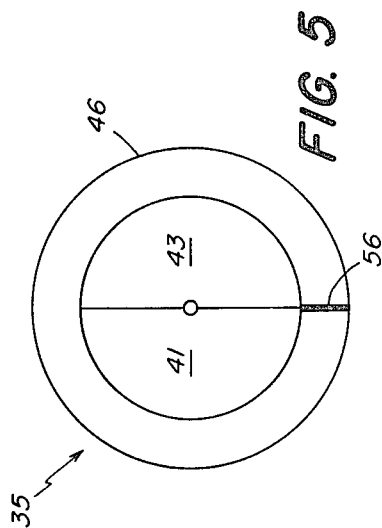
FIG. 5 is a face view showing the arrangement of a filter wheel utilized in the apparatus of FIG. 1.

In order to provide a defined starting point in the timing sequence and to remove ambiguity, the filter wheel also carries an opaque strip 56, e.g. a strip of tape, which totally occludes the light path in the interrupter module once each revolution. This is illustrated in FIG. 5. In the example illustrated, this occlusion is assumed to occur just as the red filter is coming into operative position. This arrangement is illustrated in FIG. 5. The opaque strip produces a recognizable sharp pulse in the output signal of the phototransistor 52. With reference to the signal diagrams in FIG. 3, the composite output signal from the interrupter module is represented at FIG. 3A.

Figure 4A:
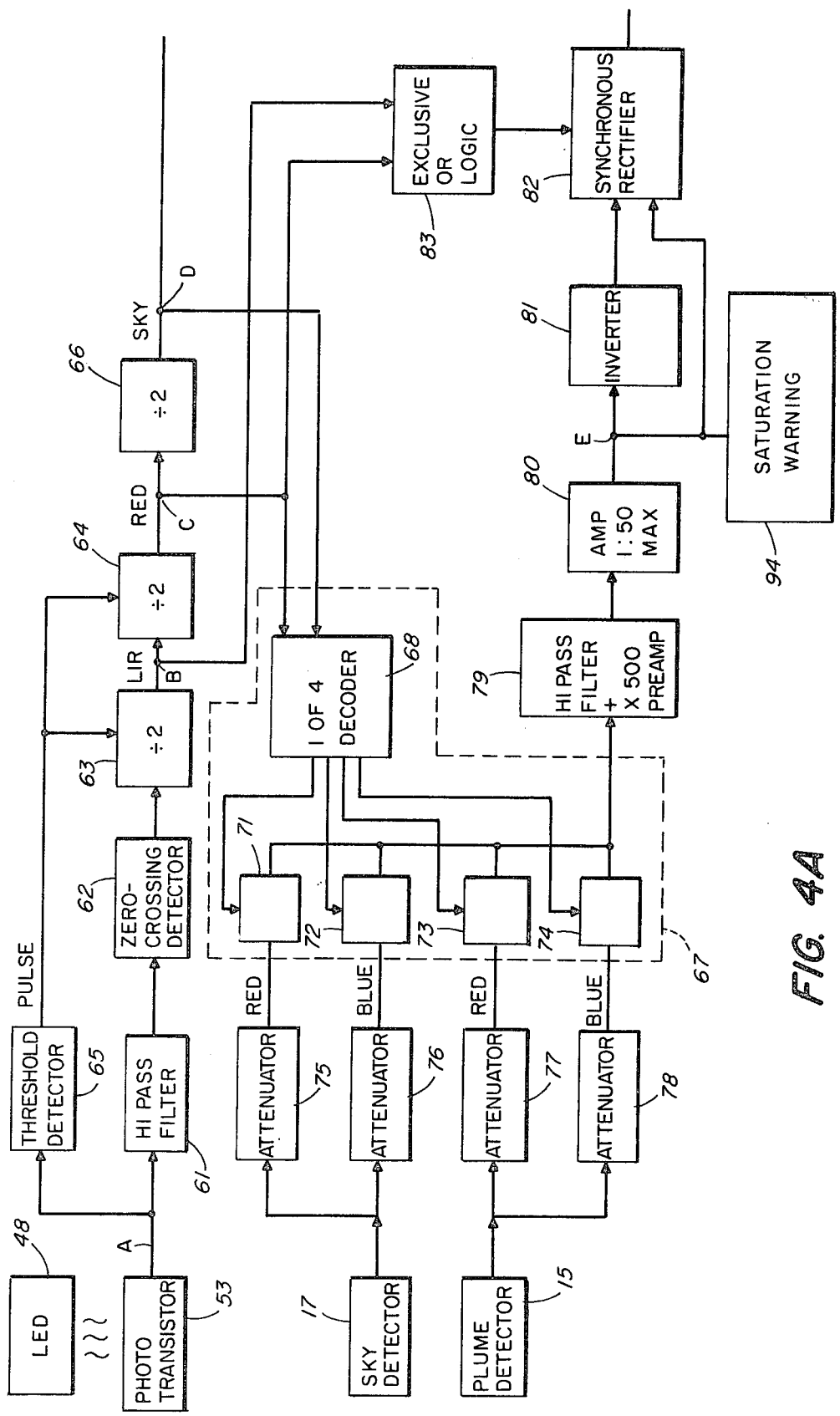
FIGS. 4A and 4B are a block diagram of signal processing circuitry employed with the apparatus of FIG. 1.
Figure 4B:
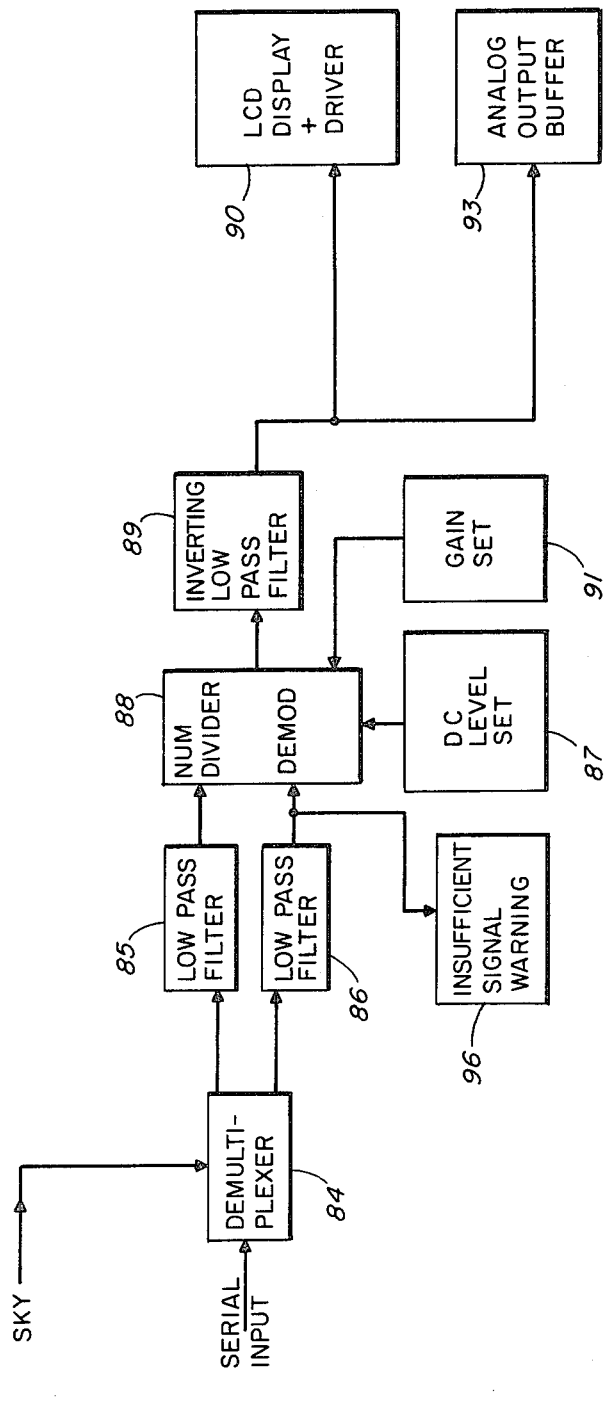

Referring now to FIG. 4, the sinusodial component from the phototransistor 52 is applied, through a high pass filter 61, to a zero crossing detector 62. This detector provides a binary or logic level signal appropriate for driving a pair of sequential divide-by-two counters 63 and 64. These counters effect division by four to yield a signal, having a 50% duty cycle, which undergoes one cycle for each revolution of the filter wheel.

Figure 3B:
Figure 3C:

The output signal from the phototransistor is also applied to a threshold detector 65 which detects the pulses produced by the opaque strip which periodically occludes the interrupter module. The threshold detector generates a corresponding logic level pulse which is applied to reset the counters 63 and 64 at that time. Thus, the phasing of the output signals from these counters will have a known relationship with the actual rotation of the color wheel despite any latent ambiguity in the sinusoidal component of the signal obtained from the phototransistor 52. The signals obtained from the counters 63 and 64 are indicated in FIGS. 3B and 3C, respectively, in FIG. 3. The phasing is such that the output signal from the counter 64 is positive (logic one) when the red filter is operative and at ground (logic zero) when the blue filter is operative.

Figure 3D:

Though both the sky detector and the plume detector could be operative during each cycle of the apparatus, i.e. during each rotation of the color wheel, the signal processing circuitry in fact handles the signals from these two detectors sequentially on alternate cycles or rotations. Treating the signal components sequentially allows all the components to be processed by a common amplification system, obviating problems in balancing gains. For use in controlling this sequential mode of operation, the output signal from the divide-by-two counter 64 is applied to a third divide-by-two counter 66. When the output signal from the counter 66 is positive, the signal from the plume detector is processed and, when it is low, the signal from the sky detector is processed. This output signal is indicated in FIG. 3D.

As indicated previously, four signal components or values are to be measured, i.e. red and blue for both the sky detector and the plume detector. These signals are selected sequentially by a multiplexer 67 controlled by timing signals taken from the counters 64 and 66. The multiplexer 67 comprises a decoder 68 which decodes the timing signals to provide four discrete interval signals, each of which controls a respective analog switch 71–74. A separate attenuator, 75–78 respectively, is provided at the input of each analog switch so the levels of the different signal components can be independently adjusted.

Figure 3E:
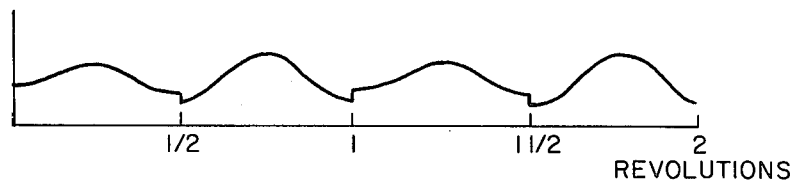

The combined sequential signal is applied to a high pass filter and preamplifier 79 having a gain of approximately 500 and then to an amplifier 80 having a gain adjustable from about 1 to 50. The amplified composite output signal, illustrated in FIG. 3E, is applied both directly and through an inverter 81 to a synchronous rectifier or switch 82. By selectively inverting or not inverting the composite output signal during selected phases, the synchronous rectifier 82 effectively performs the subtraction referenced previously, i.e. the subtraction of the red component from the blue component for each of the detectors and provides synchronous rectification, a technique which greatly reduces the contributions of noise from all frequencies other than the filter wheel rotational frequency. A control signal having the appropriate phasing for this purpose is obtained by means of an exclusive OR (XOR) gate 83 which combines the output signals from the first and second divide-by-two counters 63 and 64.

The output signal from the rectifier 82 is still a serial or sequential signal, though selected portions (representing different colors) have been reversed in polarity. Further, the composite serial sequential output signal comprises components from both the sky detector and the plume detector. Separation of these latter two constituents is performed by a demultiplexer or switch 84. The demultiplexer 84 is controlled by the output signal from the counter 66.

The separated signals provided by the demultiplexer 84, each of which is derived from a respective one of the detectors, are provided to respective low pass filters 85 and 86. Each of these filters provides a d.c. voltage which is proportional to the average amplitude of the respective signal component. In each case, since the blue component was previously inverted by the synchronous rectifier or switch 82, the d.c. component will be essentially proportional to the difference between the respective blue and red components. These d.c. signals are applied to a divider 88 which takes their quotient. Divider 88 operates, in accordance with known techniques, to provide an increasingly positive signal as the quotient increases. In order to cause this signal to increase in a negative direction, and to provide a longer filter time constant, divider 88 is followed by an inverting low pass filter 89. A d.c. output level adjustment 87 is also incorporated in the divider circuitry so that the movement of the output signal in response to an increasing quotient is with respect to an arbitrary starting point. Thus, the output signal from the inverting low pass filter 89 can represent the desired mathematical function of the input parameters. In the present case, the starting point is set at a preselected positive voltage representing unity or 100% transmission. As the quotient increase, i.e., toward unity, the output signal drops toward zero, representing complete opacity. A gain adjustment allows compensation for gain drifts of the detectors.

The output signal then is provided to appropriate readout circuitry 90 for display and through an analog output buffer 93 for recording. A digital voltmeter having a liquid crystal readout is a particularly effective form of display for a portable, battery operated form of the apparatus. The output display preferably also includes warning indicators for signalling that various internal signals are at inappropriate levels for obtaining an accurate reading. In particular, it is desirable to sense the amplitude of the signal from the amplifier 80, e.g. by means of a suitable detector as indicated at 94, to provide a warning if saturation might occur due to too large a signal amplitude. Likewise, a threshold detector 96 responsive to the output signal from filter 86 can provide a useful warning indication if the value of that signal drops to a level so low that an inaccurate division would result. Such a condition could occur if there were, for example, insufficient polarization of the background light to effect the measurements in accordance with the present invention.

Adjustment and Operation

In setting up the instrument, the attenuators 75–78 are adjusted so that all four signal components are equal when the apparatus is aimed at a source of polarized white light large enough so that both photodetectors are equally illuminated. These adjustments compensate for any difference between the two photodetectors, differences in density between the red and blue filters, and the non-uniformities in the spectral responses of the detectors. In the field, but before the actual measurements are begun, the instrument is preferably aimed at a uniform area of sky which is generally in the direction of the smoke plume but without the plume being within the field of view. This is done so that both measurement detectors experience essentially the same illumination.

At this time, the gain adjustment 91 affecting the output signal from the divider circuit 88 is adjusted so as to provide a zero output signal, i.e. one indicating 100% transmission. As will be understood, this reading corresponds to a plume of zero opacity, i.e. no plume at all, and thus sets the initial calibration of the instrument. At this time, the variable gain amplifier 80 and the half-wave plate 12 are also adjusted so that sufficient signal is present but saturation does not occur.

Once this initial calibration is performed, the apparatus is aimed, using the eyepiece 21 with the mirror 23 in place, so that an image is obtained as illustrated in FIG. 2. As described previously, this aiming assures that, when the mirror 23 is removed, light from the plume will fall on the detector 15 while light from an adjacent area of sky falls on the detector 17. At this time, the zoom lens 11 may be adjusted to cause the image to appropriately fill the reticle in the manner illustrated.

When the mirror is then withdrawn, following aiming, the signal processing circuitry described above extracts the four a.c. signal components derived from the two detectors and processes them to yield an output signal which varies substantially in accordance with the following function.

$$1 - \frac{I_{pb} - I_{pr}}{I_{sb} - I_{sr}}$$

As to the fractional component of this expression, the numerator in effect represents that portion of the blue polarized component of light coming from the plume which exceeds that portion of the blue owing to white polarized light. In other words, subtracting the red component nullifies that part of the blue which is due to a balanced or white light. As explained previously, this compensation tends to negate the effect of direct illumination of the plume itself, as distinct from light coming through the plume. The denominator of the fractional component of the above expression represents the same treatment of light coming from the background sky. Thus, the fraction in general can be thought to represent the proportion of polarized blue light which originates with the background sky and passes through the plume. As indicated previously, the fractional part itself thus represents transmissivity whereas the measurement usually desired is one of opacity. Accordingly, this normalized fraction is subtracted from unity as indicated to yield a value which is indicative of opacity.

While the terms "red" and "blue" have been used in the foregoing description for convenience, it should be understood that these terms are meant in a relative sense, i.e. to describe a two color measurement scheme in which one measurement is taken over a shorter wavelength band than the other. Thus, no very particular color limitation is intended.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. The method of determining the opacity of a smoke plume comprising:

measuring the polarized component of light received from the plume;

measuring the polarized component of light received from an area of sky adjacent the sky; and normalizing the value obtained from the plume in relation to the value obtained from the adjacent sky area, the normalized value so obtained being indicative of the transmissivity of the plume.

2. The method as set forth in claim 1 wherein only the blue components from the plume and adjacent sky area are measured.

3. The method of determining the opacity of a smoke plume comprising:

measuring the polarized blue component of light received from the plume;

measuring the polarized blue component of light received from an area of sky adjacent the sky;

taking the difference between said measurements; and normalizing said difference in relation to the intensity of light received from the adjacent sky area, the normalized difference so obtained being indicative of the opacity of the plume.

4. The method of determining the opacity of a smoke plume comprising:

measuring the polarized blue component of light received from the plume;

measuring the polarized red component of light received from the plume;

taking the difference between the blue and red plume light components;

measuring the polarized blue component of light received from an area of sky adjacent the plume;

measuring the polarized red component of light received from said sky area;

taking the difference between the blue and red sky light components; and generating a signal which is proportional to the ratio of the first difference value to the second difference value, said signal being indicative of the transmissivity of said plume.

5. The method of determining the opacity of atmospheric pollutants in the presence of ambient polarized skylight comprising:

measuring the polarized blue component of light received from an area of sky containing pollutants;

measuring the polarized red component of light received from said area;

taking the difference between the blue and red measured light values; and normalizing the difference value in relation to the sky brightness, the normalized difference so obtained being indicative of the transmissively through the pollutants.

6. The method as set forth in claim 5 wherein said differences is normalized by being divided by the value by which the blue polarized component of skylight exceeds the red polarized component of skylight.

7. Apparatus for measuring the opacity of atmospheric pollutants in the presence of ambient polarized skylight, said apparatus comprising:

optical means for collecting, separately, light from a first direction in which said pollutants produce significant occlusion of the skylight and light from a second direction in which said pollutants produce substantially less occlusion of the skylight;

polarized filter means for selectively passing components of the light samples;

detector means for generating an electrical signal which is responsive to the polarized content of the light samples passed by said filter means;

means for rotating the effective angle of polarization of said filter means thereby to cause the electrical signal generated by said detector means to include an a.c. component which is responsive to the degree of polarization of the light samples; and signal processing means interconnected with said detector means for obtaining a measurement which is responsive to the ratio of the average rectified a.c. signal components produced by the respective samples, said measurement being thus indicative also of the opacity of the pollutants.

8. Apparatus for measuring the opacity of a smoke plume, said apparatus comprising:

a first photodetector;

a second photodetector adjacent said first photodetector;

lens means for forming an image at the plane of said detectors so that light from a smoke plume to be studied falls on said first detector and light from an adjacent sky area falls on said second detector;

rotating filter means interposed in the light paths approaching said detectors, said rotating filter means including a polarizing element which effects modulation of the polarized component of light impinging on said detectors and including also color selective filter segments which are sequentially interposed to cause said detectors to be alternately responsive to blue light and red light;

means for deriving a timing signal which is synchronized with the rotation of said filter means;

signal processing means controlled by said timing signal and operative upon signals generated by said photodetectors for generating a first signal which is responsive to the difference between the blue polarized light and the red polarized light received by said first photodetector and for generating a second signal which is responsive to the difference between the blue polarized light and the red polarized light received by said second photodetector, said signal processing means being also operative to generate an output signal which varies as a function of the ratio of said first signal to said second signal, the amplitude of said output signal being indicative of the opacity of said plume.

9. Apparatus for measuring the opacity of atmospheric pollutants in the presence of ambient polarized skylight, said apparatus comprising:

optical means for collecting light from a first direction in which said pollutants produce significant occlusion of the skylight and light from a second direction in which said pollutants produce substantially less occlusion of the skylight;

photodetector means responsive to the collected light;

rotating filter means interposed in the light paths approaching said detectors, said rotating filter means including a polarizing element which effects modulation of the polarized component of light impinging on said detector means;

color selective filter means for causing said detector means to be alternately responsive to blue light and red light;

signal processing means operative upon signals generated by said photodetector means for generating a first signal component ($I_{pb}$) which is responsive to the blue polarized light received from the first direction, for generating a second signal component ($I_{pr}$) which is responsive to the red polarized light received from the first direction, for generating a third signal component ($I_{sb}$) which is responsive to the blue polarized light received from the second direction and for generating a fourth signal component ($I_{sr}$) which is responsive to the red polarized light received from said second direction, said signal processing means being also operative to generate an output signal (S) which varies as the following function of the four said signal components, $$S = 1 - \frac{I_{pb} - I_{pr}}{I_{sb} - I_{sr}}$$

the amplitude of said output signal being indicative of the opacity of said atmospheric pollutants.

10. Apparatus for measuring the opacity of a smoke plume, said apparatus comprising:

photodetector means;

lens means for forming an image of an area of sky including said plume at the plane of said detector means;

rotating filter means interposed in the light paths approaching said detector, said rotating filter means including a polarizing element which effects modulation of the polarized component of light impinging on said detector means;

color selective filter means for causing said detector means to be alternately responsive to blue light and red light;

signal processing means operative upon signals generated by said photodetector means for generating a first signal component ($I_{pb}$) which is responsive to the blue polarized light received from the plume, for generating a second signal component ($I_{pr}$) which is responsive to the red polarized light received from the plume, for generating a third signal component ($I_{sb}$) which is responsive to the blue polarized light received from an area of sky adjacent the plume and for generating a fourth signal component ($I_{sr}$) which is responsive to the red polarized light received from said sky area, said signal processing means being also operative to generate an output signal (S) which varies as the following function of the four said signal components, $$S = 1 - \frac{I_{pb} - I_{pr}}{I_{sb} - I_{sr}}$$

the amplitude of said output signal being indicative of the opacity of said plume.

* * * * *